(12) United States Patent
Uutela et al.

(10) Patent No.: US 10,674,424 B2
(45) Date of Patent: Jun. 2, 2020

(54) METHOD AND APPARATUS FOR MEASURING PHYSIOLOGICAL PARAMETERS

(71) Applicant: GENERAL ELECTRIC COMPANY, Schenectady, NY (US)

(72) Inventors: Kimmo Henrik Uutela, Helsinki (FI); Hanna Elina Viertio-Oja, Espoo (FI)

(73) Assignee: General Electric Company, Schenectady, NY (US)

( * ) Notice: Subject to any disclaimer, the term of this patent is extended or adjusted under 35 U.S.C. 154(b) by 366 days.

(21) Appl. No.: 14/968,067

(22) Filed: Dec. 14, 2015

(65) Prior Publication Data

US 2016/0192122 A1 Jun. 30, 2016

(30) Foreign Application Priority Data

Dec. 30, 2014 (GB) .................................. 1423354.8

(51) Int. Cl.
*H04W 40/20* (2009.01)
*A61B 5/00* (2006.01)
*H04W 4/80* (2018.01)

(52) U.S. Cl.
CPC .......... *H04W 40/20* (2013.01); *A61B 5/6887* (2013.01); *A61B 5/742* (2013.01); *H04W 4/80* (2018.02)

(58) Field of Classification Search
CPC combination set(s) only.
See application file for complete search history.

(56) References Cited

U.S. PATENT DOCUMENTS

| | | | | | |
|---|---|---|---|---|---|
| 5,549,113 | A | * | 8/1996 | Halleck | G08B 21/0453 600/484 |
| 5,676,690 | A | * | 10/1997 | Noren | A61N 1/36564 607/9 |
| 6,198,394 | B1 | * | 3/2001 | Jacobsen | A61B 5/1112 340/573.1 |

(Continued)

FOREIGN PATENT DOCUMENTS

| | | |
|---|---|---|
| WO | 2011076884 A2 | 6/2011 |
| WO | 2011109716 A2 | 9/2011 |
| WO | 2012125425 A2 | 9/2012 |

OTHER PUBLICATIONS

Combined Search and Exam Report for corresponding GB Appln. No. 1423354.8, dated Jun. 26, 2015, 7 pages.

*Primary Examiner* — Zhiyu Lu

(57) ABSTRACT

A method and device for calculating at least a first type and a second type of physiological parameter with a wireless measuring device adapted to acquire patient physiological data, the wireless measuring device is configured to operate in at least a first and a second operating mode for processing the physiological data. The method comprises acquiring with the wireless measuring device patient physiological data, and identifying a first identity for the wireless measuring device, the first identity being linked to a first context for operating the wireless measuring device. The method further comprises using the first identity to allow the wireless measuring device to operate in a first operating mode linked to the first identity, and processing the patient physiological data to calculate a first type of physiological parameter, linked to the first operating mode of the wireless measuring device.

14 Claims, 2 Drawing Sheets

(56) References Cited

U.S. PATENT DOCUMENTS

| | | | |
|---|---|---|---|
| 2002/0019584 A1* | 2/2002 | Schulze | G06F 19/3418 600/300 |
| 2004/0130446 A1* | 7/2004 | Chen | G08B 25/016 340/539.12 |
| 2004/0225199 A1* | 11/2004 | Evanyk | A61B 5/0002 600/300 |
| 2005/0020927 A1* | 1/2005 | Blondeau | A61B 5/02427 600/500 |
| 2005/0249037 A1* | 11/2005 | Kohn | A61B 5/0002 367/117 |
| 2007/0106145 A1 | 5/2007 | Kim et al. | |
| 2008/0221418 A1* | 9/2008 | Al-Ali | A61B 5/02416 600/324 |
| 2010/0331631 A1* | 12/2010 | MacLaughlin | A61B 5/14552 600/301 |
| 2012/0182143 A1* | 7/2012 | Gaines | A61B 5/0022 340/539.12 |
| 2013/0030259 A1* | 1/2013 | Thomsen | A61B 5/02028 600/301 |
| 2013/0325404 A1* | 12/2013 | Yuen | G06F 11/00 702/182 |
| 2014/0073486 A1* | 3/2014 | Ahmed | A61B 5/02405 482/9 |
| 2014/0089007 A1* | 3/2014 | Sim | G06F 19/3418 705/3 |
| 2014/0227671 A1* | 8/2014 | Olmstead | G11B 27/10 434/308 |
| 2016/0270717 A1* | 9/2016 | Luna | G16H 50/20 |

* cited by examiner

METHOD AND APPARATUS FOR MEASURING PHYSIOLOGICAL PARAMETERS

TECHNICAL FIELD

The present disclosure relates to a method and apparatus for calculating at least a first and a second physiological parameter.

BACKGROUND

Patient monitoring devices are known that are used to obtain physiological parameters of a first type that have a specific relevance for a specific first hospital environment. The same first type of physiological parameter has no specific relevance in a second hospital environment. For example, EEG and FEMG measurement technology is used to measure a parameter which is related to the depth of anesthesia during surgery. The same parameter does not provide any useful clinical information in an ICU environment.

If in a second hospital environment a second type of physiological parameter needs to be obtained, a different patient monitoring device needs to be used to obtain this second type of physiological parameter, even if the first and second type of physiological parameter are obtained by means of similar technology.

In a medical environment, like in a hospital, operators of medical devices have to work efficiently while, at the same time respecting strict and precise work procedures to ensure proper use of the medical devices and to provide proper patient care. The connection of a patient to a monitoring device can prove to be difficult and time consuming. If several different physiological parameters need to be obtained for a patient it can be difficult and frustrating for medical staff to have to connect and disconnect a series of medical devices one after the other to obtain the required parameters. This is especially true if the medical staff is under high time pressure. In practise the patient remains at a fixed location and the several medical devices are moved towards and from the patient consecutively. Alternatively, the patient is moved between locations to be able to connect the patient to the several measuring devices.

It appears that there is need for an improved method and improved devices to obtain at least a first and a second physiological parameter for a patient, which allows for more time efficient work procedures in a medical environment.

SUMMARY OF THE INVENTION

In one aspect, the present disclosure is directed to a method for calculating at least a first type and a second type of physiological parameter with a wireless measuring device adapted to acquire patient physiological data, wherein said wireless measuring device is configured to operate in at least a first and a second operating mode for processing the physiological data, the method comprising:

acquiring with the wireless measuring device patient physiological data, identifying a first identity for the wireless measuring device, the first identity being linked to a first context for operating the wireless measuring device, using the first identity to allow the wireless measuring device to operate in a first operating mode linked to said first identity, and processing the patient physiological data to calculate a first type of physiological parameter, linked to said first operating mode of the wireless measuring device.

The method can be performed in any order, for example, the connection can be done after the identification.

In another aspect, the present disclosure is directed to a computer readable medium storing computer-executable instructions, which, when executed by a computer cause the computer to perform each of the method steps of the method according to the disclosure.

In yet another aspect, the present disclosure is directed to a wireless measuring device for measuring at least a first and a second type of physiological parameter, the wireless measuring device comprising:

at least one sensor adapted to acquire patient physiological data, a processor for processing said patient physiological data to obtain patient physiological parameters, wherein said processor is configured to operate in at least a first operating mode for processing said patient physiological data to obtain a first type of physiological parameter and a second operating mode to obtain a second type of physiological parameter, a controller, connected to the processor, for instructing the processor to operate in a selected operating mode of said at least first and second operating modes, the controller being connected to a receiver for receiving a control signal relating to a determined identity for the wireless measuring device linked to a context for operating the wireless measuring device, wherein the controller is configured to receive said control signal to select an operating mode relating to the determined identity for the wireless measuring device.

At least one of the above embodiments provides one or more solutions to the problems and disadvantages with the background art. Other technical advantages of the present disclosure will be readily apparent to one skilled in the art from the following description and claims. Various embodiments of the present application obtain only a subset of the advantages set forth. No one advantage is critical to the embodiments. Any claimed embodiment may be technically combined with any other claimed embodiment(s).

BRIEF DESCRIPTION OF THE DRAWINGS

The accompanying drawings illustrate presently exemplary embodiments of the disclosure and serve to explain, by way of example, the principles of the disclosure.

DETAILED DESCRIPTION

In the present disclosure, the word "context" is used to indicate the environment wherein the wireless measuring device is used. The context wherein the measuring device is used can depend on a specific apparatus in the vicinity of the wireless measuring device, which apparatus is adapted to communicate with the wireless measuring device. Alternatively, the context wherein the wireless measuring device is used can be linked to the physical area wherein the wireless measuring device is used and which is identified using an identifier which is positioned, for instance, in the room wherein the wireless measuring device is present.

Yet another possibility for providing a specific context is the presence of a person who is capable of operating the wireless measuring device or who is capable of interpreting parameters obtained using the wireless measuring device. This person can be provided with a tag adapted to communicate with the wireless measuring device, in order to allow identification of a context.

In the present disclosure the word "identity" is used to refer to a parameter or value which can be used, after processing of said parameter or value, to determine a distinct operating mode for a device selected from a series of optional operating modes.

Figure 1:
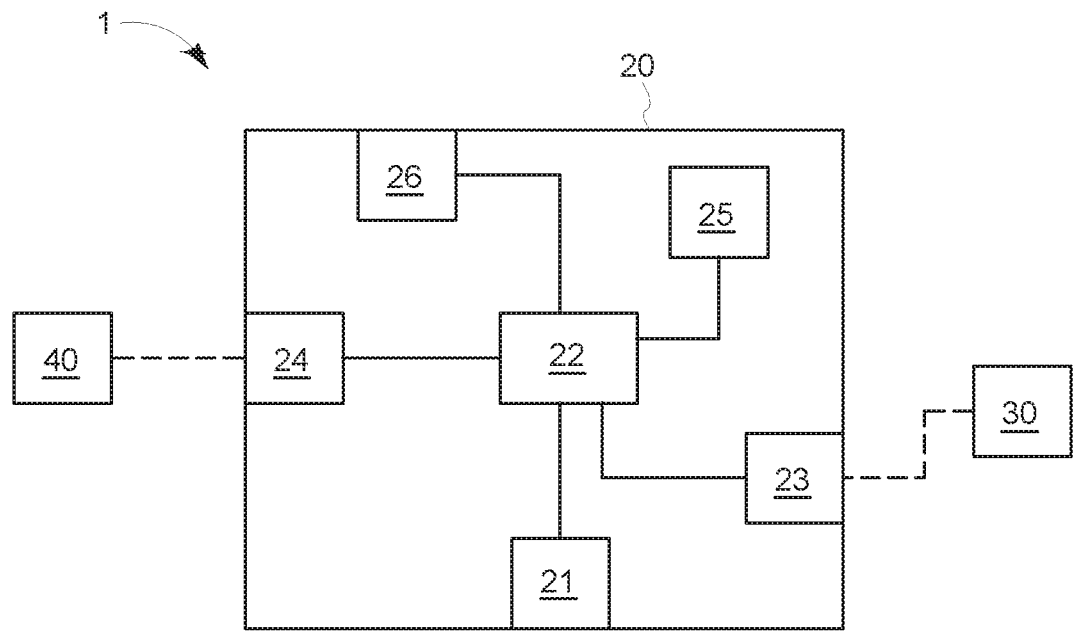
FIG. 1 is a diagrammatic illustration of a wireless measuring device according to a first exemplary embodiment of the disclosure.

FIG. 1 is a diagrammatic illustration of a wireless measuring device 1 according to a first exemplary embodiment of the disclosure. The wireless measuring device 1 is provided with a housing 20 which forms the exterior of the wireless measuring device 1.

The housing 20 of the wireless measuring device 1 is adapted to be connected to a patient 10, wherein the patient 10 is a human being or a mammal whose physiological parameters are to be obtained. The wireless measuring device 1 can be physically in contact with the patient 10 or can be positioned at a distance from patient 10, wherein the distance allows for the measuring of physiological parameters of the patient 10.

The wireless measuring device 1 is configured to identify a first identity for the wireless measuring device 1, wherein the first identity is linked to a first context wherein the wireless measuring device 1 is used. The first identity allows the wireless measuring device 1 to operate in a first operating mode associated with said first context to calculate a first type of physiological parameter.

The wireless measuring device 1 comprises at least one sensor 21, adapted to acquire at least a first type of patient physiological data. Alternatively, a first sensor and a second sensor (not shown) can be used in the wireless measuring device 1 wherein the first sensor and the second sensor are adapted to measure a first type and a second type of patient physiological data respectively.

To allow processing of the patient physiological data acquired with the sensor 21, the wireless measuring device 1 comprises a controller 22, adapted to control the different components of the device 1 and to allow the device 1 to operate in a selected operating mode.

The wireless measuring device 1 further comprises a receiver 24, configured to communicate using a wireless communication protocol with an electronic device 40 and to receive from said electronic device 40 information relating to at least a first identity for the wireless measuring device 1.

According to an embodiment of the present disclosure, the receiver 24 is configured for communication with a stationary device, wherein the wireless measuring device 1 and the stationery device are configured for communication using any adapted communication protocol. According to a first example, the communication could comprise WIFI or a similar communication protocol. According to another example, the communication protocol could be Bluetooth®. According to yet another example, Near Field Communication (NFC) protocol could be used.

According to an embodiment of the present disclosure, the receiver 24 is configured for communicating with a stationery device in the form of a transmitter.

As shown in FIG. 1, the receiver 24 is connected to the controller 22 for processing the data received with the receiver 24 to allow the controller 22 to determine from this data an identity and to use said identity to operate the wireless measuring device 1 in a selected operating mode.

The controller 22 is provided with a processor. The controller 22 is further provided with or connected to a memory 25. The memory 25 can be used to store data received from the sensor 21 and/or received from the receiver 24. The memory 25 can also be used to store data relating to preselected operating modes for the wireless measuring device 1 in the form of a table. In case such a table is used, the data received from the receiver 24 can be processed and compared with data stored in the table using the controller 22 to determine an operating mode for the wireless measuring device 1.

The wireless measuring device 1 further comprises a power source 26 to provide electrical power for the different components of the wireless measuring device 1. The power source 26 comprises, for example, a rechargeable battery.

The controller 22 is adapted to process the signal received from the electronic device 40 to thereby determine a selected identity for the wireless measuring device 1. Once the selected identity has been determined, the controller 22 can instruct the processor to process the patient physiological data acquired with the sensor 21 to calculate physiological parameters of a type related to said selected identity for the wireless measuring device 1.

The wireless measuring device 1 further comprises a transmitter 23. The transmitter 23 is adapted to send physiological data acquired with the sensor 21 to an electronic device 30, configured to receive and process said physiological parameter. The transmitters 23 and 30 are adapted to communicate using a wireless communication protocol.

The electronic device 30 is, for instance, a medical device 30 which is used in combination with the wireless measuring device 1. Such a medical device could be used to provide an output for monitoring and/or diagnostic purposes.

In the embodiment according to FIG. 1 the transmitter 23 is connected with the sensor 21 via the controller 22. This means that the data acquired with the sensor 21 can be processed by the controller 22 before the parameters are forwarded to the transmitter 23.

Figure 2:
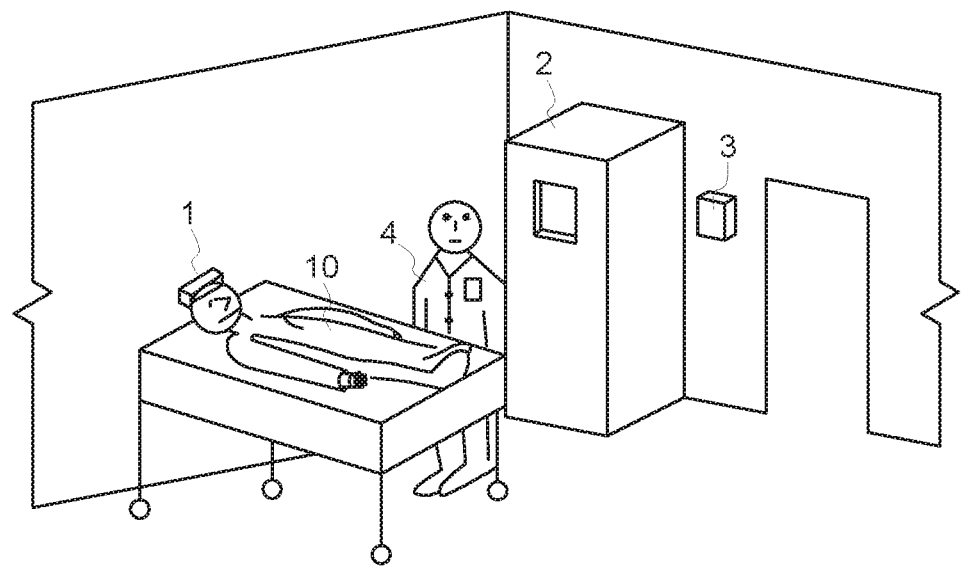
FIG. 2 is a diagrammatic illustration of a the use of a wireless measuring device according to an exemplary embodiment of the disclosure in a first context.

In the example of FIG. 2, use of the wireless measuring device 1 is shown in a first context. The wireless measuring device 1 can obtain a first identity after communication using a wireless communication protocol with an electronic device. This electronic device is, for example, the medical device 2 in combination with which the wireless measuring device 1 is used, an identifier 3 which is linked to the specific area wherein the wireless measuring device 1 is present, or the presence of a person 4 equipped with a device which allows wireless communication such as an electronic tag.

Figure 3:
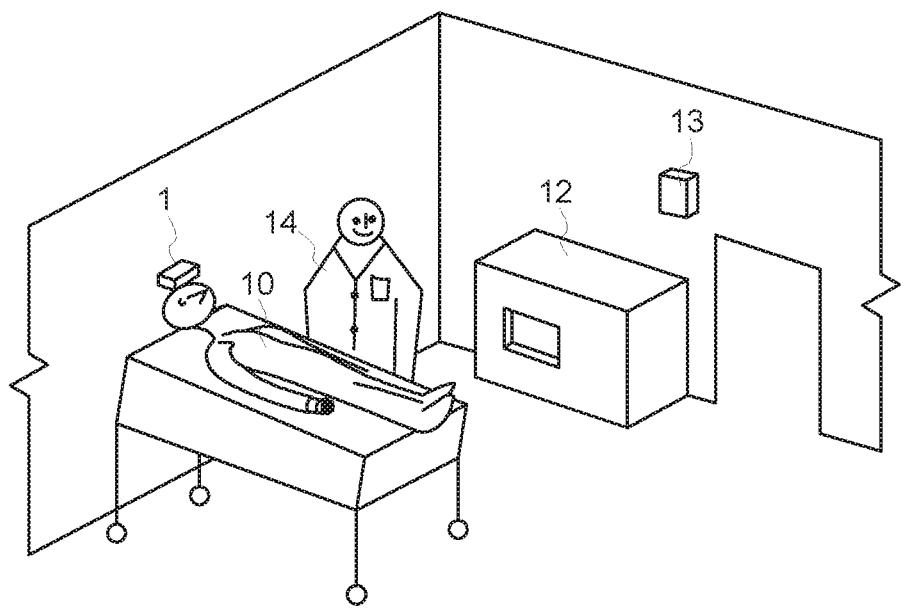
FIG. 3 is a diagrammatic illustration of the use of the wireless measuring device in a second context.

In FIG. 3, a diagrammatic illustration of the use of the wireless measuring device 1 in a second context is shown. The wireless measuring device 1 remains connected to the patient 10 to allow the wireless measuring device 1 to acquire patient physiological data. The context wherein the wireless measuring device 1 according to FIG. 3 is used differs from the context as shown in FIG. 2. This means, for instance, that the apparatus 12 in combination with which the wireless measuring device 1 is used has changed. It is also possible that the identifier 13 changes. This indicates that the patient 10 and the wireless measuring device 1 have been moved from a first to a second geographical location, such as a different room in a hospital. It also possible that the context according to FIG. 3 has changed since the person 14 present in the vicinity of the patient 10 has taken over the position from the person 4 (see FIG. 2).

It should be noted that it is possible that a combination of changes leads to a modified context.

According to the present disclosure, the wireless measuring device 1 is adapted to identify in the second context, as shown in FIG. 3, a second identity. The second identity for the wireless measuring device 1 is linked to the second context wherein the wireless measuring device 1 is used. The second identity allows the wireless measuring device 1 to operate in a second operating mode associated with said second context for operating the wireless measuring device 1 and allows calculation of a second type of physiological parameter, linked to said second operating mode of the wireless measuring device 1.

As shown by means of FIG. 2 and FIG. 3, according to the present disclosure, the wireless measuring device 1 is adapted in a first context according to FIG. 2 to acquire patient physiological data. The same wireless measuring device 1 is adapted, without requiring any modification or intervention, to operate in a second context, which is different from the first context, in a different operating mode. In the second context the wireless measuring devices 1 will obtain similar patient physiological data as the patient physiological data acquired in the first context. In the first context, the acquired patient physiological data will be processed using a first operating mode to calculate a first type of physiological parameter; in the second context the patient physiological data will be processed using a second operating mode to calculate a second type of physiological parameter.

The technical effect of these measures is that the same measuring device 1 can be used in different contexts to calculate a first and a second physiological parameter instead of requiring use of specific measuring devices each of which is specific to a context wherein the measuring device is used. Therefore, the wireless measuring device 1 can be used on the same patient 10 throughout a workflow comprising a number of different and independent actions.

This means that the wireless measuring device 1 is connected to the patient 10 and is used to first obtain patient physiological data and to calculate a first type of physiological parameter. Thereafter, the wireless measuring device 1 is not disconnected nor modified and the obtained patient physiological data are used to calculate a second type of physiological parameter. This functionality will improve medical procedures and will improve efficiency when a first and a second type of physiological parameter needs to be obtained.

According to an embodiment of the disclosure, the wireless measuring device 1 enables different physiological parameters to be obtained using similar technology. For example, a wireless measuring device 1 can be used for EEG and FEMG measurements to obtain a value describing the depth of anesthesia during surgery in an operating room. The operating room represents a first context for the use of the wireless measuring device 1. After completion of surgery, the patient 10 and the wireless measuring device 1 can be transferred together to, for example, an ICU environment. In such an ICU environment, the same wireless measuring device 1 is adapted to obtain similar patient physiological parameters which are processed to calculate a parameter relevant for ICU purposes.

Figure 4:
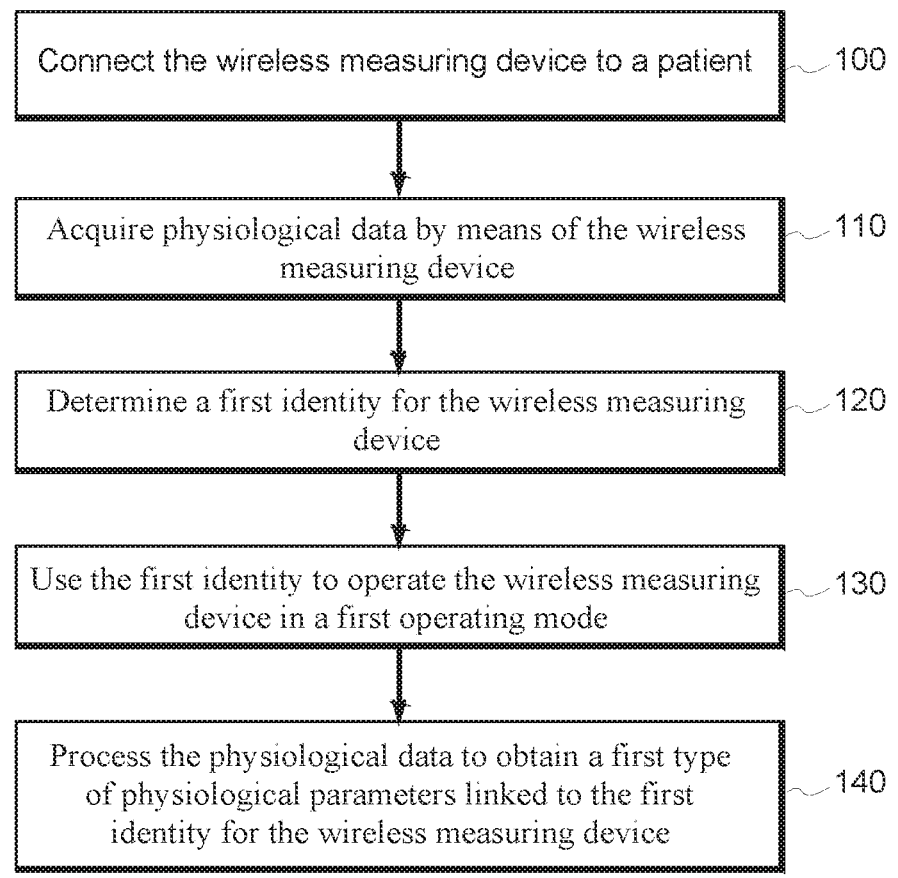
FIG. 4 shows a flow chart of the method for operating a wireless measuring device according to an exemplary embodiment of the disclosure.

FIG. 4 shows a flow chart of the method for operating a wireless measuring device 1 according to a first exemplary embodiment of the disclosure. In a first step 100, the wireless measuring device 1 is connected to a patient. In a second step 110, the wireless measurement device 1 is used to acquire patient physiological data. In a third step 120, a first identity for the wireless measurement device 1 is determined, wherein the first identity is linked to a first context for operating the wireless measuring device 1. While the exemplary embodiment shows steps, the steps can be taken in any order as long as they make technical sense. For example the determination of the identity in the third step 120 can be made before the first step 100.

In a fourth step 130, the first identity is used to allow the measuring device 1 to operate in a first operating mode. This first operating mode allows for processing of the patient physiological data to obtain a first type of physiological parameter linked to the first identity for the wireless measuring device 1. The processing of the physiological data is represented in fifth step 140 in FIG. 4.

According to an example of the present disclosure, the wireless measuring device 1 operates in a first operating mode until the wireless measuring device 1 receives data relating to a specific identity for the wireless measuring device 1 which will cause the wireless measuring device 1 to adopt a further operating mode linked to this specific identity.

According to a further embodiment, the wireless measuring device 1 is configured to be in a state for receiving an identity prior to authorizing operation in a specific operating mode for calculation of physiological parameters.

According to an embodiment of the present disclosure, the wireless measuring device 1 has a default operating mode, wherein the wireless measuring device 1 will adopt an alternative operating mode if and when a specific identity has been received by means of wireless communication with an electronic device 40. The device 1 is configured to return to its default operating mode when communication between the wireless measuring device 1 and the electronic device 40 is ended or interrupted.

In a further embodiment of the measuring device 1 according to the present disclosure, the wireless measuring device 1 comprises a display for displaying the operating mode of the wireless measuring device. The display provides information to allow an operator such as the person 4 or 14 in FIG. 3 and FIG. 4 to visually determine and check in which operating mode the wireless measuring device 1 is operating.

According to an embodiment of the present disclosure, the wireless measuring device 1 is provided with an application which allows the wireless measuring device 1 to produce an output relating to possible movement of the wireless measuring device 1.

According to a first alternative, the wireless measuring device 1 comprises a movement detector, such as a gyroscope, adapted to generate an output corresponding to possible movement of the wireless measuring device 1.

According to an alternative embodiment, the wireless measuring device 1 comprises a positioning detection application such as a geographical positioning system (GPS) which is adapted to produce an output corresponding to a change in said geographical position of the wireless measuring device 1.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. Method for calculating at least a first type of physiological parameter and a second type of physiological parameter with a wireless measuring device adapted to acquire patient physiological data, the method comprising:
   acquiring with the wireless measuring device patient physiological data;
   determining a geographical location where the wireless measuring device is being used;
   in response to the geographical location being a first geographical location, operating the wireless measuring device in a first operating mode linked to the first geographical location where the patient physiological data is processed to calculate the first type of physiological parameter; and
   in response to the geographical location being a second geographical location, operating the wireless measuring device in a second operating mode linked to the second geographical location where the patient physiological data is processed to calculate the second type of physiological parameter, wherein the patient physiological data processed in the first and second operating modes are of the same type, and the second type of physiological parameter is different than the first type of physiological parameter.

2. Method according to claim 1, wherein the wireless measuring device is configured to communicate with at least one stationary device, the method further comprising:
   establishing communication between the wireless measuring device and the at least one stationary device to thereby generate a communication signal, and
   using the communication signal to determine the geographical location for the wireless measuring device.

3. Method according to claim 2, wherein the wireless measuring device and the at least one stationary device are configured for communicating using Near Field Communication (NFC) protocol.

4. Method according to claim 2, wherein the stationary device is a transmitter.

5. Method according to claim 1, wherein the wireless measuring device comprises a transmitter, wherein the method comprises:
   sending, by the transmitter, the obtained physiological parameters to an electronic device adapted to receive said physiological parameters.

6. Non-transitory computer readable medium storing computer-executable instructions, which, when executed by a computer cause the computer to:
   receive patient physiological data from a wireless measuring device;
   determine a geographical location where the wireless measuring device is being used;
   in response to the geographical location being a first geographical location, operate the wireless measuring device in a first operating mode linked to the first geographical location where the patient physiological data is processed to calculate the first type of physiological parameter; and
   in response to the geographical location being a second geographical location, operate the wireless measuring device in a second operating mode linked to the second geographical location where the patient physiological data is processed to calculate the second type of physiological parameter, wherein the patient physiological data processed in the first and second operating modes are of the same type, and the second type of physiological parameter is different than the first type of physiological parameter.

7. A wireless measuring device for measuring at least a first type of physiological parameter and a second type of physiological parameter, the wireless measuring device comprising:
   at least one sensor adapted to acquire patient physiological data;
   a receiver adapted to receive a control signal relating to a geographical location where the wireless measuring device is being used; and
   a controller adapted to:
      in response to the geographical location being a first geographical location, operating the wireless measuring device in a first operating mode linked to the first geographical location where the patient physiological data is processed to calculate the first type of physiological parameter; and
      in response to the geographical location being a second geographical location, operating the wireless measuring device in a second operating mode linked to the second geographical location where the patient physiological data is processed to calculate the second type of physiological parameter, wherein the patient physiological data processed in the first and second operating modes are of the same type, and the second type of physiological parameter is different than the first type of physiological parameter.

8. Wireless measuring device according to claim 7, wherein the wireless measuring device comprises a transmitter for sending the obtained physiological parameter to an electronic device configured to receive said parameter.

9. Wireless measuring device according to claim 7, wherein the receiver is configured to communicate with at least a first stationary device that generates the control signal.

10. Wireless measuring device according to claim 7, wherein the receiver is configured for communicating using Near Field Communication (NFC) protocol.

11. Wireless measuring device according to claim 7, wherein the wireless measuring device further comprises a display for displaying the first or second operating mode of the wireless measuring device.

12. Wireless measuring device according to claim 7, wherein the wireless measuring device comprises a movement detection application configured to generate an output corresponding to a movement of the wireless measuring device.

13. Wireless measuring device according to claim 7, wherein the wireless measuring device comprises a positioning detection application configured to generate an output corresponding to the geographical location of the wireless measuring device.

14. Method according to claim 1, wherein the first type of physiological parameter includes a depth of anesthesia during surgery, and the second type of physiological parameter is relevant for ICU purposes after the surgery.

* * * * *